(12) United States Patent
Kotidis

(10) Patent No.: US 8,086,266 B2
(45) Date of Patent: Dec. 27, 2011

(54) CELL PHONE BASED MEMS FOURIER TRANSFORM INFRARED (FTIR) GAS SENSORS

(75) Inventor: Petros Kotidis, Framingham, MA (US)

(73) Assignee: Block Engineering, LLC, Marlborough, MA (US)

( * ) Notice: Subject to any disclaimer, the term of this patent is extended or adjusted under 35 U.S.C. 154(b) by 384 days.

(21) Appl. No.: 12/350,486

(22) Filed: Jan. 8, 2009

(65) Prior Publication Data
US 2009/0227287 A1 Sep. 10, 2009

Related U.S. Application Data

(60) Provisional application No. 61/019,735, filed on Jan. 8, 2008.

(51) Int. Cl.
*H04M 1/00* (2006.01)
(52) U.S. Cl. .................................... 455/556.1
(58) Field of Classification Search .............. 455/556.1, 455/90.3, 90.1, 66.1
See application file for complete search history.

(56) References Cited

U.S. PATENT DOCUMENTS

| 7,693,687 B2* | 4/2010 | Lev-Ami et al. ............... 702/186 |
| 7,702,108 B2* | 4/2010 | Amon et al. .................. 380/270 |
| 2003/0136837 A1* | 7/2003 | Amon et al. .................. 235/435 |
| 2006/0279732 A1* | 12/2006 | Wang et al. .................. 356/326 |
| 2008/0045825 A1* | 2/2008 | Melker et al. ................ 600/365 |
| 2010/0284017 A1* | 11/2010 | Reyes et al. .................. 356/452 |
| 2010/0309454 A1* | 12/2010 | Zhang ............................. 356/39 |

FOREIGN PATENT DOCUMENTS
GB 2436660 A * 10/2007
* cited by examiner

*Primary Examiner* — Lewis West
(74) *Attorney, Agent, or Firm* — Houston Eliseeva, LLP

(57) ABSTRACT

A cell-phone based chemical sensor and communication/data management system has cell phones that are each provided with an integrated sensor (sensor enabled cell phone). Each cell phone comprises an infrared spectrometer for spectrally analyzing the ambient environment and a communication portion for communicating with the cellular phone network and transmitting data from the infrared spectrometer over the cellular network. These cell phones are linked to each other and a central server via the routing nodes of the cellular phone network.

15 Claims, 2 Drawing Sheets

CELL PHONE BASED MEMS FOURIER TRANSFORM INFRARED (FTIR) GAS SENSORS

RELATED APPLICATIONS

This application claims the benefit under 35 USC 119(e) of U.S. Provisional Application No. 61/019,735, filed on Jan. 8, 2008, which is incorporated herein by reference in its entirety.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
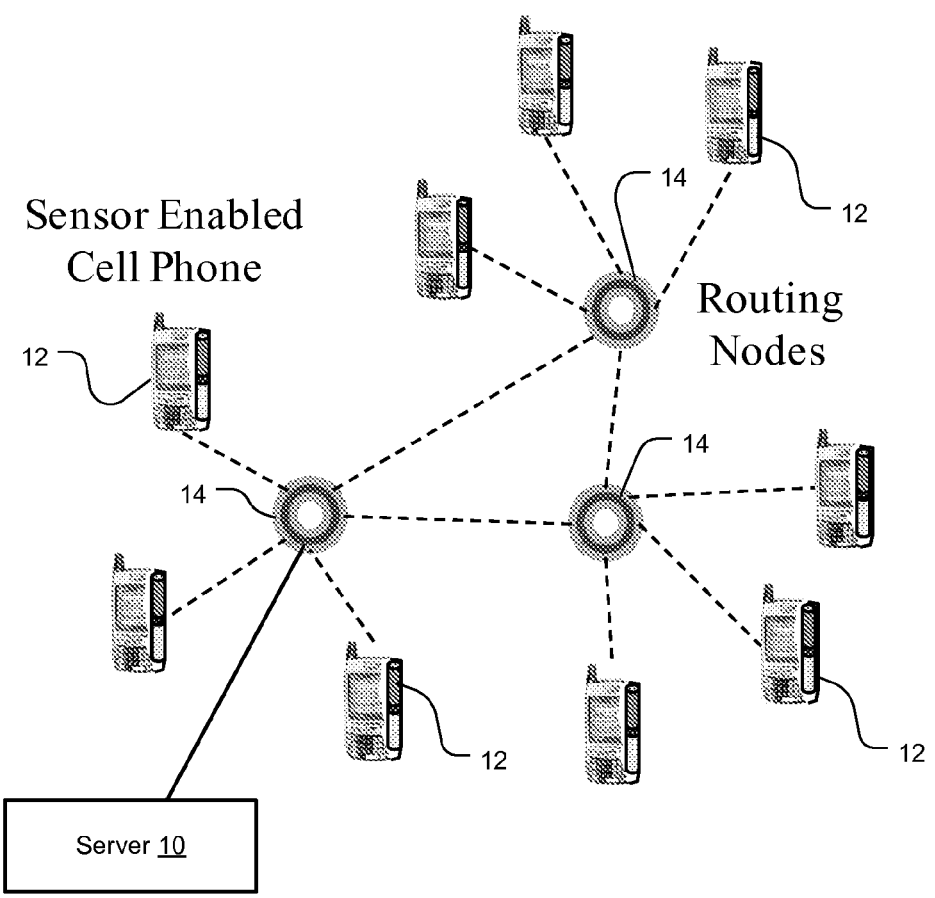
FIG. 1 is a schematic view of a cellular phone network of sensor enabled cell phones according to the present invention.

A cell-phone based chemical sensor and communication/data management system constructed according to the principles of the present invention is shown in FIG. 1. This platform provides a potential million-level nodes network by leveraging the cellular phone network.

According to the invention each cell phone 12 is provided with an integrated sensor (sensor enabled cell phone). Each cell phone 12 includes an infrared spectrometer for spectrally analyzing the ambient environment and a communication portion for communicating with the cellular phone network and transmitting data from the infrared spectrometer over the cellular network. These cell phones are linked to each other and a central server 10 via the routing nodes of the cellular phone network.

The routing nodes 14 and/or central server 10 employ data fusion and management. Managing the huge amount of data that the network generates requires significant in-network processing to prevent possibly detrimental traffic congestion. The nodes also employ anomaly detection. One non-trivial task of data fusion is the determination of anomalous measurements to alert the proper authorities. Few spatially dispersed abnormal measurements may simply mean that the corresponding sensors are malfunctioning while many spatially concentrated abnormal measurements may indicate a serious event too late to respond. Statistically significant early trends in the data are detected to minimize false alarms and misdetection probabilities.

Recently, microelectromechanical systems (MEMS) sensors have been developed for detection of chemical agents and toxic industrial gases. One example is the compact MEMS sensor described in U.S. patent application Ser. No. 11/966,594, entitled Miniature Fourier Transform Spectrometer and Method of Operation, filed on Dec. 28, 2007, which is incorporated herein by this reference in its entirety.

This is a high-performance, pen-sized Fourier transform infrared MEMS spectrometer having low power consumption and potentially low cost. A unique advantage of FTIR technology, developed over many years of experience in analytical instruments, is its high specificity and low false alarm rate.

In more detail, the arms of the Michelson interferometer of this FTIR are integrated on a common micro-optical MEMS optical bench using surface micromachine technology.

In this MEMS FTIR, sensitivity is increased by attaching a miniature gas preconcentrator to the FTIR sensor. Preconcentrators using a novel technology based on Self-Assembled Monolayers on Mesoporous Supports (SAMMS) in one example. Further, communication electronics are used in order to allow for seamless integration with the cell-phone core processing chips into the cellular phone/data network.

This sensor enabled cell phone network has advantages for homeland security applications.

Common platform integration: The C sensor enable cell phones are integrated into the common cell phone DSP (digital signal processing) architecture. There is no need for the phone to call the network; in the preferred embodiment, the network employs periodic polling and "registration request" channels for low level information transfer. User enabled operation: The sensor may be activated or disabled by a user in seconds. Low cost and easy maintenance: MEMS are inherently low cost devices. All solid state operation requires no user intervention, minimal maintenance and replaceable accessories. Location, date, time and readings: Standard cell phone tower triangulation (enhanced 911) or existing GPS global positioning system) technologies will provide location, date and time information. Warning from operations centers: Standard cell phone technology using broadcast mode warns the user and motivates running in "activated" mode. Wide range of sensing environments: FTIR technology allows the detection of essentially all dangerous gases with one sensor. The sensor preferably meets the military's Joint Chemical Agent Detector (JCAD) specs, e.g., sensitivity to G-Agent at 1 mg/m3.

In a preferred embodiment, the sensor enabled cell phones also detect volatile organic biomarkers, possibly associated with exposure to or infection from bioweapons. Sample collection: Preconcentrator technology allows for increased sensitivity and more accurate readings. Multiple samples: FTIR software deals with multiple gases. The system is able to identify certain liquids and solids with disposable attachments. Due to FTIR sensor's small size, space exists within the cell phone to add biological or radiological sensors. Power profile: To conserve power the sensor is in low power mode until a dangerous substance is detected. Preferably power management techniques (sampling, date batching, on-off control) are used to maintain a 10-20 mW steady state power consumption. Environmental conditions: FTIR sensor technology is capable of mil spec performance compatible with the JCAD requirements. Lifetime: Standard lifetime for the MEMS FTIR sensor and preconcentrator strips exceeds one year; the strips (at 1000 times concentration gain) are virtually permanently reusable. Development architectures: Use of a MEMS development platform enables low cost prototyping and, once developed, allows for high volume, wide deployment of such sensors.

Figure 2:
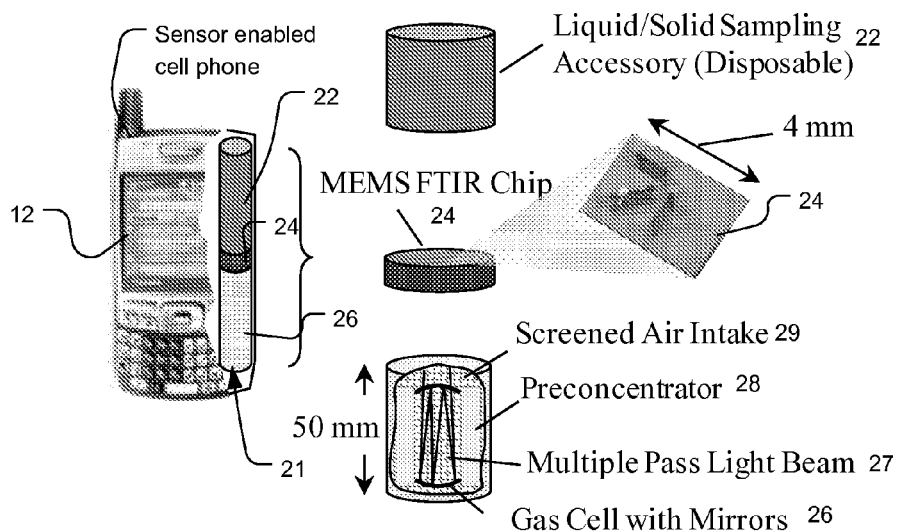
FIG. 2 is a schematic view showing the construction of the sensor enabled cell phone according to the present invention.

FIG. 2 shows the sensor enabled cell phone 12. The sensor component 21 includes preferably a disposable liquid/sampling accessory 22 that serves as a mechanical and optical interface to the sample. The sensor 21 further includes the MEMS Michelson interferometer of the FTIR sensor (MEMS FTIR chip 24) as described in the incorporated Ser. No. 11/966,594 application, published as US 2010/0284017. The drawing insert is a SEM picture of erected MEMS mirrors used to define the arms of the Michelson interferometer of the FTIR sensor.

The sensor 21 includes a gas cell 26 with mirrors to provide a multiple pass light beam 27 within the gas cell 26. The preconcentrator 28 is included within the gas cell 26 to increase sensitivity. A screened air intake 29 allows ambient air to enter the gas cell 26.

In the preferred embodiment, the MEMS FTIR Chip 24 is combined with: (a) preconcentrator interface, (b) compact gas cell design, (c) special packaging, (d) electronic interface, power control and data management. The preconcentrator strips and multi-pass cell increase sensitivity by many orders of magnitude. The top of the sensor 21 could have an optional disposable accessory 22 for liquid/solid sampling, if needed for more trained users.

Figure 3:
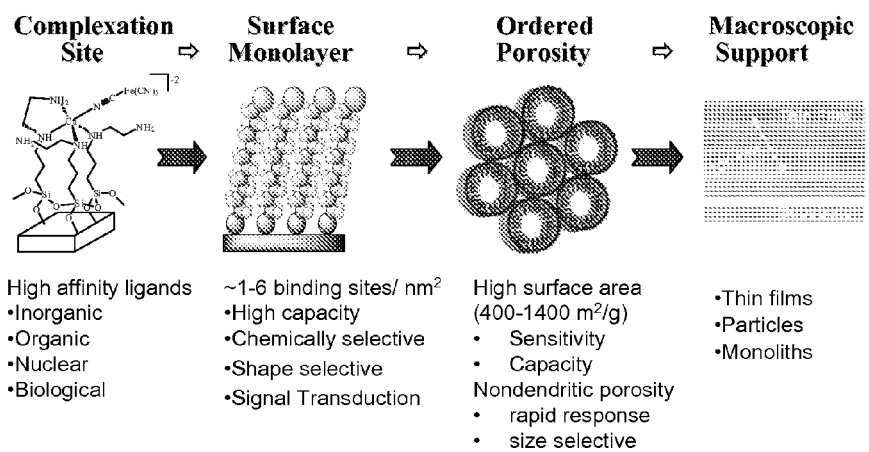
FIG. 3 are schematic views showing exemplary preconcentrators.

The materials used in the preconcentrator are self-assembled monolayers on mesoporous supports (SAMMS) as illustrated in FIG. 3. The physical structure and surface chemistry can be application tailored. High affinity and selective surface chemistry allows selective capture of the signature compound(s) of interest while the vast majority of matrix interference compounds will pass through the sorbent unretained. Because of the high purity of the captured fraction, subsequent analysis steps, which result in high confidence identification of trace concentrations, is greatly simplified. This enables the use of the MEMS chip while creating a highly sensitive system. The initial effort will focus on G-class nerve agents for which we will use SAMMS materials recently developed and competitively tested. After an extensive literature search was completed, hundred of new sorbents were created for the capture of G-class nerve agents (and their hydrolysis products). For existing and novel materials the sorbent affinity, selectivity and stability were evaluated. However the best surface chemistries for the capture of Dimethyl Methyl Phosphonate (DMMP) from air (and water) were identified and further developed.

At the network and data management level, power management is used to conserve power. Preferably, intelligent sampling and data batching methods are employed, as well as intelligent on-off control in data transmission mechanisms. For localization, outdoor location of a reporting unit is reported either cell phone GPS or the 911-location system. For indoors, where these techniques are not operable, a WiFi-based indoor localization system is used in one example.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cell phone network, comprising:
    cell phones;
    a server; and
    network routing nodes for routing information between the cell phones and the server,
    one or more of the cell phones being sensor enabled cell phones that each include an infrared spectrometer sensor for spectrally analyzing gases in an ambient environment about the sensor enabled cell phone, and
    a communication portion for communicating with the cell phone network and transmitting data collected from the infrared spectrometer over the cell phone network each said infrared spectrometer sensor comprising:
    a microelectromechanical MEMS based Fourier transform infrared chip;
    an air intake allowing ambient air to enter the gas cell; and
    a gas cell with mirrors to provide a multiple pass light beam.

2. The cell phone network of claim 1 wherein the infrared spectrometer sensor further comprises a disposable liquid sampling accessory serving as a mechanical and optical interface for liquid samples.

3. The cell phone network of claim 1 wherein the infrared spectrometer sensor further comprises a disposable solid sampling accessory serving as a mechanical and optical interface for solid samples.

4. The cell phone network of claim 1 wherein the sensor comprises a pre-concentrator that is located within a gas cell to increase sensitivity of gas identification.

5. The cell phone network of claim 1 wherein said infrared spectrometer sensor is completely enclosed within a casing of the sensor enabled cell phone.

6. The cell phone network of claim 1 wherein the server employs data fusion and management within the cell phone network.

7. The cell phone network of claim 1 wherein the air intake allows ambient air to enter the gas cell that operates within a casing of the sensor enabled cell phone without a cable or collection head attached to or external to the sensor enabled cell phone.

8. The cell phone network of claim 1 wherein the server or network routing nodes employ periodic polling of said sensor enabled cell phones in the cell phone network and provide low level information transfer along registration request channels.

9. The cell phone network of claim 1 wherein date and time of data collection is provided along with location information from cell phone tower triangulation or global positioning systems.

10. The cell phone network of claim 1 wherein a warning to a user to operate in activated mode is transmitted in broadcast mode over the cell phone network in response to a predetermined condition.

11. The cell phone network of claim 1 wherein the infrared spectrometer sensor further detects volatile organic biomarkers associated with exposure to or infection from bioweapons.

12. The cell phone network of claim 1 further comprising a radiological sensor within a casing of the sensor enabled cell phones.

13. The cell phone network of claim 1 wherein the spectrometer includes a Michelson interferometer with arms integrated on a common micro-optical MEMS optical bench using surface micromachine technology.

14. The cell phone network of claim 1 wherein the network routing nodes analyze statistical trends of said data collected from the infrared spectrometer to minimize mis-detection probabilities.

15. A cell phone comprising:
    a housing:
    a communications section within said housing for communications on a cell phone network; and
    a pen-sized cylindrical infrared spectrometer within said housing comprising a microelectromechanical MEMS based Fourier Transform Infrared FTIR chip, a gas cell with mirrors to provide a multiple pass light beam, a pre-concentrator to increase sensitivity of gas identification, and a screened air intake allowing ambient air to enter the gas cell,
    wherein said gas spectrometer identifies gases resident in the ambient air within the gas cell and said communications section transmits said gas identifying information on the cell network.

* * * * *